(12) United States Patent
Rossi et al.

(10) Patent No.: US 7,820,800 B2
(45) Date of Patent: Oct. 26, 2010

(54) PROCESS FOR THE PURIFICATION OF IL-18 BINDING PROTEIN

(75) Inventors: Mara Rossi, Rome (IT); Thierry Ziegler, Leognan (FR); Laure Valognes, Talence (FR)

(73) Assignee: Ares Trading S.A., Aubonne (CH)

(*) Notice: Subject to any disclaimer, the term of this patent is extended or adjusted under 35 U.S.C. 154(b) by 0 days.

(21) Appl. No.: 10/576,372

(22) PCT Filed: Nov. 4, 2004

(86) PCT No.: PCT/EP2004/052807

§ 371 (c)(1), (2), (4) Date: Apr. 19, 2006

(87) PCT Pub. No.: WO2005/049649

PCT Pub. Date: Jun. 2, 2005

(65) Prior Publication Data

US 2007/0037734 A1 Feb. 15, 2007

Related U.S. Application Data

(60) Provisional application No. 60/517,447, filed on Nov. 5, 2003.

(30) Foreign Application Priority Data

Nov. 5, 2003 (EP) .................................. 03104092

(51) Int. Cl.
C07K 14/715 (2006.01)
C07K 14/00 (2006.01)
C12N 9/02 (2006.01)
A23J 1/00 (2006.01)

(52) U.S. Cl. ..................... 530/413; 530/350; 530/344; 530/412; 530/417

(58) Field of Classification Search ....................... None
See application file for complete search history.

(56) References Cited

U.S. PATENT DOCUMENTS

| | | |
|---|---|---|
| 2007/0134761 A1 | 6/2007 | Chatellard et al. |
| 2007/0196895 A1 | 8/2007 | Aloni et al. |
| 2007/0258962 A1 | 11/2007 | Chatellard et al. |
| 2007/0293658 A1 | 12/2007 | Kornmann et al. |
| 2008/0076708 A1 | 3/2008 | Altarocca et al. |
| 2008/0199913 A1* | 8/2008 | Weber et al. ............... 435/70.1 |
| 2008/0200658 A1* | 8/2008 | Le Strat et al. ............. 530/413 |

FOREIGN PATENT DOCUMENTS

| | | |
|---|---|---|
| EP | 1 110 969 A1 | 6/2001 |
| WO | WO 99/09063 A1 | 2/1999 |
| WO | WO 2004/081167 A2 | 9/2004 |
| WO | WO 2004/101617 A1 | 11/2004 |
| WO | WO 2005/040384 A1 | 5/2005 |
| WO | WO 2005/083058 A1 | 9/2005 |
| WO | WO 2006/003134 A1 | 1/2006 |
| WO | WO 2006/128908 A1 | 12/2006 |
| WO | WO 2006/131550 A1 | 12/2006 |

OTHER PUBLICATIONS

Boschetti, E., Antibody separation by hydrophobic charge induction chromatography, 2002, Trends in Biotechnology, vol. 20, Issue 8, pp. 333-337.*

Xiang et al., Determination of the functional epitopes of human interleukin-18 binding protein by site-directed mutagenesis, 2001, The Journal of Biological Chemistry, vol. 276, No. 20, pp. 17380-17386.*

Burton et al., 1998, Hydrophobic charge induction chromatography: salt independent protein adsorption and facile elution with aqueous buffer, Journal of Chromatography A, vol. 814, pp. 71-81.*

Kim, S-H. et al. "Structural requirements of six naturally occurring isoforms of the IL-18 binding protein to inhibit IL-18" *Proceedings of the National Academy of Sciences of USA*, Feb. 1, 2000, pp. 1190-1195, vol. 97, No. 3.

Altschul, S.F. et al. "Basic local alignment search tool" *J. Mol. Biol.*, 1990, pp. 403-410, vol. 215.

Altschul, S.F. et al. "Gapped BLAST and PSI-BLAST: a new generation of protein database search programs" *Nucleic Acids Research*, 1997, pp. 3389-3402, vol. 25, No. 17.

Boschetti, E. et al. "Separation of antibodies by liquid chromatography" Sep. Sci & Tech. 2, 2000, No. 15, pp. 536-632, Academic Press.

Boschetti, E. et al. "Bioprocess Tutorial Hydrophobic charge-induction chromatography" *Genetic Engineering*, Jul. 2000, vol. 20, No. 13.

Devereux, J. et al. "A comprehensive set of sequence analysis programs for the VAX" *Nucleic Acids Research*, 1984, pp. 387-395, vol. 12, No. 1.

Grantham, R. "Amino acid difference formula to help explain protein evolution" *Science*, Sep. 6, 1974, pp. 862-864, vol. 185.

Novick, D. et al. "Interleukin-18 binding protein: a novel modulator of the Th1 cytokine response" *Immunity*, Jan. 1999, pp. 127-136, vol. 10.

Pearson, W.R. et al. "Rapid and sensitive sequence comparison with FASTP and FASTA" *Methods in Enzymology*, pp. 63-98, vol. 183. 1990.

Porath, J. et al. "Metal chelate affinity chromatography, a new approach to protein fractionation" *Nature*, Dec. 18, 1975, pp. 598-599, vol. 258.

Porath, J. et al. "Immobilized metal ion affinity adsorption and immobilized metal ion affinity chromatography of biomaterials. Serum protein affinities for Gel-Immobilized iron and nickel ions" *Biochemistry*, 1983, pp. 1621-1630, vol. 22.

Puren, A. J. et al. "Gene expression, synthesis, and secretion of interleukin 18 and interleukin 1β are differentially regulated in human blood mononuclear cells and mouse spleen cells" *Proc. Natl. Acad. Sci. USA*, Mar. 1999, pp. 2256-2261, vol. 96.

(Continued)

*Primary Examiner* — Robert Landsman
*Assistant Examiner* — Ian Dang
(74) *Attorney, Agent, or Firm* — Saliwanchik, Lloyd & Saliwanchik

(57) ABSTRACT

The invention relates to a process for the purification of IL-18 binding protein (IL-18BP) from a fluid comprising hydrophobic charge-induction chromatography.

18 Claims, 2 Drawing Sheets

OTHER PUBLICATIONS

Urushihara, N. et al. "Elevation of serum interleukin-1 levels and activation of kupffer cells in biliary atresia" *Journal of Pediatric Surgery*, Mar. 2000, pp. 446-449, vol. 35, No. 3.

Vigers, G. P. A. et al. "Crystal structure of the type-I interleukin-1 receptor complexed with interleukin-1β" *Nature*, Mar. 13, 1997, pp. 190-194, vol. 386.

* cited by examiner

PROCESS FOR THE PURIFICATION OF IL-18 BINDING PROTEIN

This application is the U.S. National stage application of International Patent Application No. PCT/EP2004/052807, filed Nov. 4, 2004, which claims the benefit of U.S. patent application Ser. No. 60/517,447, filed Nov. 5, 2003, the disclosures of which are hereby incorporated by reference in their entireties, including all figures, tables and amino acid or nucleic acid sequences.

FIELD OF THE INVENTION

The present invention is in the field of protein purification. More specifically, it relates to the purification of IL-18 binding protein (IL-18BP) via hydrophobic charge-induction chromatography. Preferably, the invention further comprises purification steps selected from immobilized metal ion affinity chromatography, ion exchange chromatography, hydrophobic interaction chromatography and reverse phase chromatography.

BACKGROUND OF THE INVENTION

Proteins have become commercially important as drugs that are also generally called "biologicals". One of the greatest challenges is the development of cost effective and efficient processes for purification of proteins on a commercial scale. While many methods are now available for large-scale preparation of proteins, crude products, such as body fluids, contain not only the desired product but also impurities which are difficult to separate from the desired product. Moreover, biological sources of proteins usually contain complex mixtures of materials.

Biological sources such as cell culture supernatants of cells expressing a protein product in a recombinant way may contain less impurities, in particular if the cells are grown in serum-free medium. However, the health authorities request high standards of purity for proteins intended for human administration. In addition, many purification methods may contain steps requiring application of low or high pH, high salt concentrations or other extreme conditions that may jeopardize the biological activity of a given protein. Thus, for any protein it is a challenge to establish a purification process allowing for sufficient purity while retaining the biological activity of the protein.

Ion exchange chromatographic systems have been used widely for separation of proteins primarily on the basis of differences in charge. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution).

Anion exchangers can be classified as either weak or strong. The charge group on a weak anion exchanger is a weak base, which becomes de-protonated and, therefore, looses its charge at high pH. DEAE-cellulose is an example of a weak anion exchanger, where the amino group can be positively charged below pH~9 and gradually loses its charge at higher pH values. Diethylaminoethyl (DEAE) or diethyl-(2-hydroxy-propyl)aminoethyl (QAE) have chloride as counter ion, for instance.

A strong anion exchanger, on the other hand, contains a strong base, which remains positively charged throughout the pH range normally used for ion exchange chromatography (pH 1-14). Q-sepharose (Q stands for quaternary ammonium) is an example for a strong anion exchanger.

Cation exchangers can also be classified as either weak or strong. A strong cation exchanger contains a strong acid (such as a sulfopropyl group) that remains charged from pH 1-14; whereas a weak cation exchanger contains a weak acid (such as a carboxymethyl group), which gradually loses its charge as the pH decreases below 4 or 5. Carboxymethyl (CM) and sulphopropyl (SP) have sodium as counter ion, for example.

Chromatographic systems having a hydrophobic stationary phase have also been widely employed in the purification of proteins. Included in this category are hydrophobic interaction chromatography (HIC) and reversed phase liquid chromatography (RPLC). The physicochemical basis for separation by HIC and RPLC is the hydrophobic effect, proteins are separated on a hydrophobic stationary phase based on differences in hydrophobicity.

In HIC, generally, sample molecules in a high salt buffer are loaded on the HIC column. The salt in the buffer interacts with water molecules to reduce the solvation of the molecules in solution, thereby exposing hydrophobic regions in the sample molecules which are consequently adsorbed by the HIC column. The more hydrophobic the molecule, the less salt needed to promote binding. Usually, a decreasing salt gradient is used to elute samples from the column. As the ionic strength decreases, the exposure of the hydrophilic regions of the molecules increases and molecules elute from the column in order of increasing hydrophobicity. Sample elution may also be achieved by the addition of mild organic modifiers or detergents to the elution buffer. HIC is reviewed e.g. in Protein Purification, 2d Ed., Springer-Verlag, New York, pgs 176-179 (1988).

In HIC, different chromatographic supports are available carrying various ligands. The ligands differ with respect to their hydrophobicity. Commonly used hydrophobic ligands are phenyl-, butyl- or octyl- residues.

Hydrophobic charge-induction chromatography is a subset of HIC using resins carrying ligands such as 4-mercaptotheylpyridine derivatives. An example for a Hydrophobic charge-induction chromatography resin is MEP-HyperCel® (Boschetti et al., Genetic Engineering Vol. 20, No. 13, July, 2000, Boschetti and Jungbauer, 2000).

Reverse phase chromatography is a protein purification method closely related to HIC, as both are based upon interactions between solvent-accessible non-polar groups on the surface of biomolecules and hydrophobic ligands of the matrix. However, ligands used in reverse phase chromatography are more highly substituted with hydrophobic ligands than HIC ligands. While the degree of substitution of HIC adsorbents may be in the range of 10-50 μmoles/mL of matrix of C2-C8 aryl ligands, several hundred μmoles/mL of matrix of C4-C8 alkyl ligands are usually used for reverse phase chromatography adsorbents.

Hydrophobic interaction chromatography and reverse phase chromatography are also distinct in that hydrophobic interaction chromatography is performed in aqueous solvent conditions and changes in ionic strength are used to elute the column. The protein typically binds in the native state via hydrophobic groups located on the surface of the protein, and the native state is retained during the elution conditions. In contrast to this, reverse phase chromatography utilizes a hydrophobic solvent (typically acetonitrile) and the binding of a ligand is a function of the phase partition between the hydrophobic nature of the solvent and column functional group. Proteins are typically denatured to some extent in such solvents and bind due to the hydrophobic nature of the entire polypeptide sequence. Since the majority of hydrophobic groups are located in the core of globular proteins, the binding is related to the extent of denaturation of the protein and the accessibility of these groups to the column functional groups.

The Source 30RPC column is a polymeric reverse phase matrix. It is based on rigid, monosized 30 micron diameter polystyrene/divinyl benzene beads. Its characteristics can be summarized as follows: Exceptionally wide pH range (1-12), high selectivity, high chemical resistance, high capacity and high resolution at high flow rates.

A further type of chromatography widely used for protein purification is called immobilized metal ion affinity chromatography (IMAC). In 1975, Porath introduced immobilized metal ion affinity chromatography (IMAC) for fractionating proteins [J. Porath, J. Carlsson, I. Olsson, and G. Belfrage, *Nature* (London) 258, 598-599 (1975)]. In Porath's work, IMAC consists of derivatizing a resin with iminodiacetic acid (IDA) and chelating metal ions to the IDA-derivatized resin. The proteins are separated on the basis of their affinity for metal ions, which have been immobilized by chelation. Proteins bind to the metal ions through unoccupied coordination sites and are immobilized on the column. Since then, other ligands than IDA were used to chelate metal ions to resins. Studies with serum proteins have shown IMAC to be an extremely specific and selective separation technique [J. Porath and B. Olin, *Biochemistry* 22, 1621-1630 (1983)]. The adsorbent is prepared by coupling a metal chelate forming ligand, such as, iminodiacetic acid, to Sepharose or superose and treating it with a solution of one or more divalent metal ions such as $Zn^{2+}$, $Cu^{2+}$, $Cd^{2+}$, $Hg^{2+}$, $Co^{2+}$, $Ni^{2+}$, or $Fe^{2+}$. The binding reaction is pH dependent and elution is carried out by reducing the pH and increasing the ionic strength of the buffer or by including EDTA in the buffer.

The actual mechanisms which give rise to the binding of proteins to free metal ions are not well understood and are dependent upon a number of factors, not the least of which is the conformation of the particular protein. However, when the metal ions are immobilized, at least three limiting factors come into play, namely reduced number of available coordination sites on the metal, restricted accessibility of the tethered metal to the binding sites on the protein, and, depending upon the characteristics of the resin, limited protein access to the immobilized metal ion. Thus, it is extremely difficult a priori to state which proteins will and which will not exhibit an affinity for immobilized metal ions.

Interleukin-18 binding protein (IL-18BP) is a naturally occurring soluble protein that was initially affinity purified, on an IL-18 column, from urine (Novick et al. 1999). IL-18BP abolishes IL-18 induction of IFN-γ and IL-18 activation of NF-κB in vitro. In addition, IL-18BP inhibits induction of IFN-γ in mice injected with LPS.

The IL-18BP gene was localized to the human chromosome 11, and no exon coding for a transmembrane domain could be found in the 8.3 kb genomic sequence comprising the IL-18BP gene. Four isoforms of IL-18BP generated by alternative mRNA splicing have been identified in humans so far. They were designated IL-18BP a, b, c, and d, all sharing the same N-terminus and differing in the C-terminus (Novick et al 1999). These isoforms vary in their ability to bind IL-18 (Kim et al. 2000). Of the four human IL-18BP (hIL-18BP) isoforms, isoforms a and c are known to have a neutralizing capacity for IL-18. The most abundant IL-18BP isoform, isoform a, exhibits a high affinity for IL-18 with a rapid on-rate and a slow off-rate, and a dissociation constant (Kd) of approximately 0.4 nM (Kim et al. 2000). IL-18BP is constitutively expressed in the spleen, and belongs to the immunoglobulin superfamily. The residues involved in the interaction of IL-18 with IL-18BP have been described through the use of computer modelling (Kim et al. 2000) and based on the interaction between the similar protein IL-1β with the IL-1R type I (Vigers et al. 1997).

IL-18BP is constitutively present in many cells (Puren et al. 1999) and circulates in healthy humans (Urushihara et al. 2000), representing a unique phenomenon in cytokine biology. Due to the high affinity of IL-18BP to IL-18 (Kd=0.4 nM) as well as the high concentration of IL-18BP found in the circulation (20 fold molar excess over IL-18), it has been speculated that most, if not all of the IL-18 molecules in the circulation are bound to IL-18BP. Thus, the circulating IL-18BP that competes with cell surface receptors for IL-18 may act as a natural anti-inflammatory and an immunosuppressive molecule.

IL-18BP has been suggested as a therapeutic protein in a number of diseases and disorders, such as psoriasis, Crohn's Disease, rheumatoid arthritis, psoriatic arthritis, liver injury, sepsis, atherosclerosis, ischemic heart diseases, allergies, etc., see e.g. WO9909063, WO0107480, WO0162285, WO0185201, WO02060479, WO02096456, WO03080104, WO02092008, WO02101049, WO03013577. Given that IL-18BP is suggested as a therapeutic protein for administration e.g. to humans, there is a need for adequate amounts of IL-18BP in sufficiently high purity.

However, so far, no purification process is available that provides purified IL-18BP.

SUMMARY OF THE INVENTION

The present invention is based on the development of a purification process for IL-18 binding protein (IL-18BP).

Therefore, in a first aspect, the invention relates to the use of hydrophobic charge-induction chromatography for purification of IL-18BP.

In a second aspect, the invention relates to a process for the purification of IL-18 binding protein (IL-18BP) from a fluid comprising a step of hydrophobic charge-induction chromatography.

More specifically, the purification process of the invention further comprises a step selected from immobilized metal ion affinity chromatography, ion exchange chromatography, hydrophobic interaction chromatography and reverse phase chromatography.

DETAILED DESCRIPTION OF THE INVENTION

Figure 1:
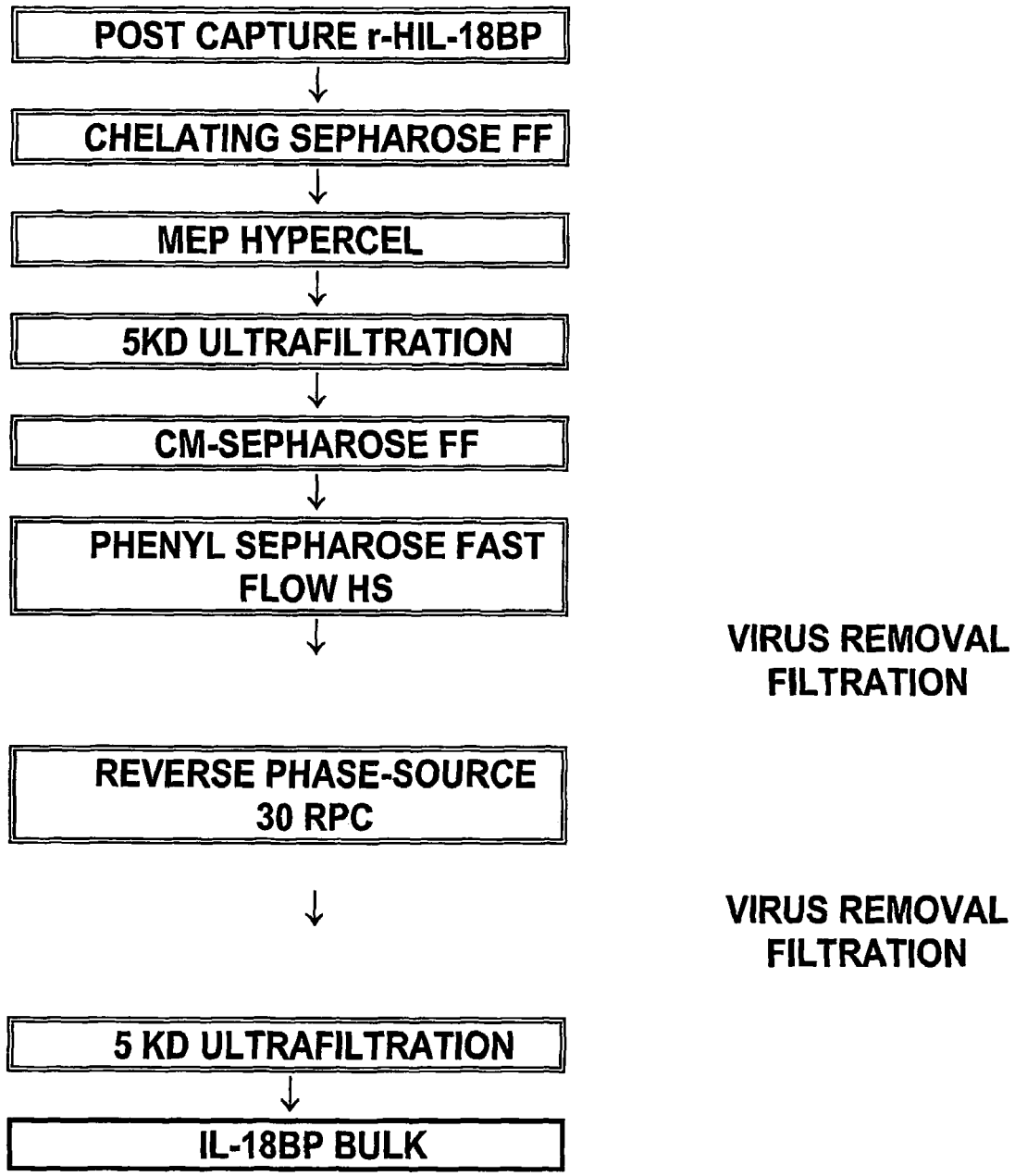
FIG. 1 shows a schematic overview over a preferred purification process of the invention, resulting in purified IL-18BP ("IL-18BP BULK").

The present invention is based on the development of a purification process for IL-18BP resulting in purified IL-18BP.

In a first aspect the invention relates to the use of hydrophobic charge-induction chromatography for purification of IL-18BP. In a preferred embodiment, this step of hydrophobic charge induction chromatography step is carried out in combination with one or more steps selected from immobilized metal ion affinity chromatography, ion exchange chromatography, hydrophobic interaction chromatography and reverse phase chromatography.

Preferably, the hydrophobic charge-induction step is carried out on a 4-mercapto-ethyl-pyridine (MEP) resin.

In a further preferred embodiment, the hydrophobic charge-induction step is carried out in combination with one or more steps selected from immobilized metal ion affinity chromatography, ion exchange chromatography, hydrophobic interaction chromatography and reverse phase chromatography. The individual chromatography steps may be carried out in any suitable order.

In a second aspect, the invention relates to a process for the purification of IL-18 binding protein (IL-18BP) from a fluid comprising a step of hydrophobic charge-induction chromatography.

The term "resin", as used herein, relates to any matrix or carrier material used in a chromatographic column, such as e.g. agarose, sepharose, superose, dextran, sephadex, polypropylene, or the like, that may be derivatized with ligands, or functional groups, such as DEAE, CM, MEP, phenyl, for example, as explained in detail in the "Background of the Invention". The matrix materials may be present in different cross-linked forms, depending on the specific use. The volume of the resin, as well as the length and diameter of column to be used depends on several parameters such as the volume of fluid to be treated, concentration of protein in the fluid to be subjected to the process of the invention, etc., and determining this is well within the skills of the person skilled in the art.

Hydrophobic charge-induction chromatography is preferably carried out on a resin having 4-mercaptoethyl-pyridine (MEP) as immobilized ligand. MEP-Hypercel® is a resin that is particularly suitable in the frame of the present invention.

Preferably, the process further contains at least one step selected from immobilized metal ion affinity chromatography, ion exchange chromatography, hydrophobic interaction chromatography and reverse phase chromatography. The individual chromatography steps may be carried out in any order. Each individual step may also be carried out more than once, if necessary.

Immobilized metal ion affinity chromatography is preferably carried out on a chelating resin, such as chelating sepharose.

The ion exchange chromatography step may contain an anion exchanger or a cation exchanger. It is preferred to use a cation exchange chromatography material, particularly a weak cation exchange material, and it is highly preferred to use a carboxymethyl (CM)-resin, such as CM sepharose FF, to carry out this step of the purification process.

The hydrophobic interaction chromatography (HIC) step may be carried out on any known HIC resin, such as a resin having alkyl- or aryl-residues as immobilized ligand. Butyl-, octyl- or phenyl-sepharose (agarose) are further examples of such HIC resins. It is preferred to use a phenyl resin, such as phenyl sepharose FF, for this step of the purification process.

The purification process may further comprise a reverse phase chromatography step. A preferred material for this step is reverse phase-source 30 RPC.

In a highly preferred embodiment, the process for purification of IL-18BP from a fluid comprises the steps of:

(a) Subjecting the fluid to immobilized metal ion affinity chromatography;

(b) Subjecting the eluate of the metal ion affinity chromatography to hydrophobic charge-interaction chromatography;

(c) Subjecting the eluate of the hydrophobic charge-interaction chromatography to cation exchange chromatography;

(d) Subjecting the flow-through of the cation exchange chromatography to hydrophobic interaction chromatography;

(e) Subjecting the eluate of the hydrophobic interaction chromatography to reverse phase chromatography.

While the order of the above steps (a) to (e) is preferred, the steps of the process of the invention may be carried out in any order that leads to a purified protein product. Any purification step of the invention may also be carried out alone (in isolation) in order to achieve some degree of purity or elimination of host cell or medium derived impurities. It is to be noted that in this preferred purification process, IL-18BP does not bind to the cation exchange resin, and thus the flow-through of this column is used for further processing. The other resins used in the frame of the purification process of the invention bind IL-18BP, while impurities do not bind. After the binding and washing steps, IL-18BP is eluted under certain conditions. In these steps, the eluate is further used, respectively.

Step (a) is preferably carried out on a chelating sepharose column, such as a chelating sepharose fast flow column, having $Zn^{2+}$ ions chelated. Preferably, binding of IL-18BP is carried out at pH 8.5±0.1, preferably in 50 mM sodium phosphate and 0.5 M NaCl having this pH. A washing step may be carried out with 15 mM ammonium chloride in equilibration buffer. Elution is preferably carried out at pH 9.0±0.5, e.g. at pH 8.7 or at pH 9, e.g. in 0.075 M ammonium acetate or in 0.06 M ammonium acetate having this pH.

Step (b) is preferably carried out on a MEP (4-mercaptoethylpyridine derivative) column, such as MEP HyperCel® (LifeSciences). Binding of IL-18BP is carried out preferably at. pH 6.1±0.1, e.g. in PBS 1X+1 NaCl having this pH. Elution is carried out preferably at pH 8.4±0.1, e.g. in with 20 mM phosphate buffer plus 35% propylene glycol, the mixture having pH 8.4±0.1.

Step (c) is preferably carried out on a carboxymethyl-sepharose (CM) column. This is a step in which the flow-through is collected for further purification. This step is based on the fact that under specific circumstances relating e.g. to salt and pH conditions, IL-18BP does not bind to the resin, while impurities (e.g. host cell proteins, serum-derived proteins) that is used for bind to it. Preferably, step (c) is carried out at pH 6.0±0.2, for example in the presence of 1 mM MES (N-morpholinoethanesulfonic acid).

Step (d) is preferably carried out on a phenyl sepharose column, such as a Phenyl-Sepahrose Fast Flow column. Preferably, binding of IL-18BP is carried out at about pH 9.1±0.2, e.g. in 50 mM sodium borate and 0.9 M ammonium sulphate or 0.10 M ammonium sulfate having this pH. The elution from the phenyl-sepharose column is preferably carried out at pH 9.1±0.2 in the presence of an elevated salt concentration, such as in 50 mM sodium borate 9.1±0.2, 0.15M ammonium sulphate having this pH.

Step (e) is preferably carried out on a Source 30 RPC column. Binding of IL-18BP to the column material is preferably carried out at pH 9.1±0.2, e.g. in 50 mM sodium borate buffer. Elution is preferably carried out using a gradient, IL-18BP eluting around 28-32% of 0,1% trifluoroacetic acid (TFA) in acetonitrile.

It is understood that the conditions described above in connection with steps (a) to (e) of the purification may also be applied when carrying out single steps of the invention, or (sub-)combinations of steps.

In a further preferred embodiment of the present purification process, one or more ultrafiltration steps are performed. Ultrafiltration is useful for removal of small molecular weight components in the eluates resulting from previous chromatographic steps. This ultrafiltration allows removing organic solvent, TFA and salts from the previous step, to equilibrate the IL-18BP in the bulk buffer and to concentrate the molecule to the desired concentration. Such ultrafiltration may e.g. be performed on ultrafiltration media excluding components having molecular weights below 5 kDa.

Preferably, ultrafiltration is carried out between steps (b) and (c), and/or after step (e). More preferably, two ultrafiltration steps are carried out, one between steps (b) and (c) and one after step (e).

If the protein purified according to the process of the invention is intended for administration to humans, it is advantageous to further include one or more steps of virus removal in the process. Preferably, a virus removal filtration step is carried out between steps (d) and (e). It is further preferred that a virus removal filtration step is carried out after step (e). More preferably, the process comprises at least two virus removal steps one of which is carried out between steps (d) and (e), the other of which is carried out after step (e).

If the initial volume of fluid from which IL-18BP is purified is large, it may be advantageous to reduce the volume of material by capturing the protein and re-suspending it in a smaller volume of buffer before actually starting the purification process.

Therefore, the process of the invention further preferably comprises an initial capture step, i.e. a step that is carried out before any of the above-mentioned purification steps and preferably before step (a) of the above process.

In a preferred embodiment, the capture step is carried out by ion exchange chromatography. Preferably, the ion exchange resin used for the capture step is a strong anion exchanger matrix, such as e.g. Q Sepharose Fast Flow. It is highly preferred to use trimethylaminoethyl-derivatized resin, such as TMAE Fractogel® (or TMAE HiCap®) as ion exchange material. Advantageously, the capture step may remove >60% of the total contaminants present in the crude material.

In order to facilitate storage or transport, for instance, the material may be frozen and thawed before and/or after any purification step of the invention.

In accordance with the present invention, IL-18BP to be purified may be native, i.e. naturally occurring IL-18BP. It may thus be purified from any natural source or material, such as e.g. from body fluids such as urine.

IL-18BP may also be derived from any animal or human source. Preferably, the IL-18BP to be purified is human, and more preferably it is recombinant IL-18BP. Recombinant IL-18BP may be produced in prokaryotic expression systems, such as in bacterial systems as Escherichia coli. It may also be produced in eukaryotic expression systems, such as yeast, insect, or mammalian cells. In accordance with the present invention, it is preferred to express IL-18BP in mammalian cells such as animal cell lines, or in human cell lines. Chinese hamster ovary cells (CHO) are an example of a cell line that is particularly suitable for expression of IL-18BP.

If IL-18BP to be purified is expressed by mammalian cells secreting it, the starting material of the purification process of the invention is cell culture supernatant, also called harvest or crude IL-18BP. If the cells are cultured in a medium containing animal serum, the cell culture supernatant also contains serum proteins as impurities.

Preferably, the IL-18BP expressing cells are cultured under serum-free conditions. In this case, the starting material of the purification process of the invention is serum-free cell culture supernatant that mainly contains host cell proteins as impurities. If growth factors are added to the cell culture medium, such as insulin, for example, these proteins will preferably be eliminated during the purification process as well.

Since IL-18BP is a soluble, secreted protein, it is released into the cell culture supernatant, either by means of its natural signal peptide, or by means of a heterologous signal peptide, i.e. a signal peptide derived from another secreted protein which may be more efficient in the particular expression system used. The fluid from which IL-18BP is purified is thus preferably cell culture supernatant, such as e.g. CHO-cell supernatant. Cell culture supernatant may comprise animal derived serum, if cells are cultured in serum containing medium. It preferred to purify the protein from the supernatant of cells that were grown in serum-free medium, i.e. in culturing medium not containing serum derived from fetal calf or other animal sources.

The term "IL-18 binding protein" is used herein synonymously with "IL-18BP". This term relates IL-18 binding proteins such as the ones defined in WO 99/09063 or in Novick et al., 1999. The term IL-18BP includes splice variants and/or isoforms of IL-18 binding proteins, as the ones defined in Kim et al., 2000, in particular human isoforms a and c of IL-18BP. The term "IL-18PB", as used herein, further includes muteins, functional derivatives, active fractions, fused proteins, circularly permutated proteins and slats of IL-18BP as defined in WO 99/09063.

The IL-18BP subject to the purification process according to the present invention may be glycosylated or non-glycosylated, it may be derived from natural sources, such as urine, or it may preferably be produced recombinantly. Recombinant expression may be carried out in prokaryotic expression systems like *E. coli*, or in eukaryotic, and preferably in mammalian, expression systems.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-18BP or encodes a viral IL-18BP (both disclosed in WO99/09063) under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nim.nih.gov) and FASTA (Pearson W R, 1990).

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mutein has at least 40% identity or homology with the sequence of either an IL-18BP or a virally-encoded IL-18BP homologue, as defined in WO 99/09063. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |

TABLE III-continued Most Preferred Groups of Synonymous Amino Acids

| Amino Acid | Synonymous Group |
|---|---|
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. 4,959,314, 4,588,585 and 4,737,462, to Mark et al; U.S. Pat. No. 5,116,943 to Koths et al., 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof. "Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

The term "salts" herein refers to both salts of carboxyl groups and to acid addition salts of amino groups of IL-18 inhibitor molecule, or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the IL-18 inhibitor, such as induction of IFN-gamma in blood cells.

The sequences of IL-18BP and its splice variants/isoforms can be taken from WO99/09063 or from Novick et al., 1999, as well as from Kim et al., 2000.

Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, described in WO 92/13095, for example. Therefore, in a preferred embodiment, the functional derivative comprises at least one moiety attached to one or more functional groups, which occur as one or more side chains on the amino acid residues. An embodiment in which the moiety is a polyethylene glycol (PEG) moiety is highly preferred.

In a further preferred embodiment of the invention, IL-18BP comprises an immunoglobulin fusion, i.e. the inhibitor of IL-18 is a fused protein comprising all or part of an IL-18 binding protein, which is fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IL-18BP, in particular the binding to IL-18. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, IL-18BP is fused to the constant region of an Ig molecule. Preferably, it is fused to heavy chain regions, like the CH2 and CH3 domains of human IgG1, for example. The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

In a third aspect, the invention relates to a protein purified by the process of purification according to the invention. In the following, such protein is also called "purified IL-18BP". Such purified IL-18BP is preferably highly purified IL-18BP. Highly purified IL-18BP is determined e.g. by the presence of a single band in a silver-stained PAGE-gel after loading of protein in the amount of 2 mcg per lane. Purified IL-18BP may also be defined as moving as a single peak in HPLC. Purified IL-18BP may also be defined as moving as a single peak in HPLC.

The IL-18BP preparation obtained from the purification process of the invention may contain less than 20% of impurities, preferably less than 10%, 5%, 3%, 2% or 1% of impurities, or it may be purified to homogeneity, i.e. being free from any proteinaceous contaminants.

Purified IL-18BP may be intended for therapeutic use, i.e. for administration to patients. If purified IL-18BP is administered to patents, it is preferably administered systemically, and preferably subcutaneously or intramuscularly, or topically, i.e. locally. Rectal or intrathecal administration may also be suitable, depending on the specific use of purified IL-18BP.

For this purpose, purified IL-18BP may be formulated as a pharmaceutical composition, i.e. together with a pharmaceutically acceptable carrier, excipients or the like.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein(s) will be a function of many variables, including the type of antagonist, the affinity of the antagonist for IL-18, any residual cytotoxic activity exhibited by the antagonists, the route of administration, the clinical condition of the patient (including the desirability of maintaining a non-toxic level of endogenous IL-18 activity).

A "therapeutically effective amount" is such that when administered, the IL-18 inhibitor results in inhibition of the biological activity of IL-18. The dosage administered, as single or multiple doses, to an individual will vary depending upon a variety of factors, including IL-18 inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

Purified IL-18BP may be used in an amount of about 0.001 to 100 mg/kg or about 0.01 to 10 mg/kg or body weight, or about 0.1 to 5 mg/kg of body weight or about 1 to 3 mg/kg of body weight or about 2 mg/kg of body weight.

In further preferred embodiments, the purified IL-18BP is administered daily or every other day or three times per week or once per week.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, purified IL-18BP can be administered prophylactically or therapeutically to an individual prior to, simultaneously or sequentially with other therapeutic regimens or agents (e.g. multiple drug regimens), in a therapeutically effective amount.

Purified IL-18BP may be used for preparation of a medicament for treatment and/or prevention of a number of diseases or disorders. Such diseases or disorders are preferably IL-18 mediated disorders. In particular, purified IL-18BP may be used for treatment and/or prevention of psoriasis, psoriatic arthritis, Crohn's Disease, rheumatoid arthritis, liver injury such as alcoholic liver cirrhosis, sepsis, atherosclerosis, ischemic heart diseases, allergies, in particular delayed-type hypersensitivity, and closed head injury.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLE 1

PURIFICATION OF RECOMBINANT, HUMAN IL-18BP FROM SERUM-FREE CHO CELL SUPERNATANT

1. Capture Step

IL-18BP present in 300 l of serum free cell culture supernatant from IL-18BP expressing CHO cells was captured on Q Sepharose FF resin. The captured material was adjusted to pH to 8.5±0.1, and conductivity to 50±5 mS/cm by adding few drops of 35% orto -phosphoric acid ($H_3PO_4$)and solid NaCl in an amount corresponding to about 0.35M.

2. Purification Process

The purification process, starting from the captured material according to above (1), is described in detail below. A flowchart of the purification process is presented in FIG. 1.

Generally, pH and conductivity values refer to values at a temperature of +25° C.

Columns were continuously monitored with UV monitors, measuring the absorbance at 280 nm.

2.1. Step a: IMAC on Chelating Sepharose Fast Flow

Equipment

Chromatographic column: XK1.6×20 cm (Amersham Biosciences);

UV monitor (optical path Length 2.5 mm) equipped with a two channel recorder (Amersham Biosciences or equivalent);

Peristaltic pump (Minipuls Gilson or equivalent);

UV Spectrophotometer (Shimadzu or equivalent);

pH meter (Metrohm or equivalent);

Conductometer (Metrohm or equivalent);

Balance (MettlerToledo or equivalent).

Materials

Chelating Sepharose Fast Flow resin (Amersham Biosciences);

Sodium Hydroxide pellets—(Merck);

Copper Sulphate (Merck);

Glacial Acetic Acid (Merck);

Ethylenediaminetetracetic acid—EDTA—(Fluka);

Sodium chloride—NaCl—Merck;

Purified water (Modulab or equivalent);

Di-Sodium hydrogen phosphate dihydrate—Merck;

Ammonium Acetate—Merck;

25% Ammonia Solution—Merck;

85%-Ortho-PhosphoricAcid—Merck;

50% Sodium Hydroxide Solution—Baker.

Buffers and Solutions

Metal charge solution: 0.2 M Copper Sulphate

Acidified water

Equilibration buffer: 50 mM Sodium phosphate pH 8.5±0.1, 0.5 M NaCl.

Elution buffer: 0.075 M Ammonium Acetate pH 9.0±0.1

Regeneration solution: 20 mM sodium phosphate pH 5.8±0.3, 0.5 M NaCl, 50 mM EDTA Sanitizing solution: 0.5 M NaOH The column was packed with Chelating Sepharose Fast Flow resin following the manufacturer's instructions. For sanitization, the column was flushed with at least 3 BV of NaOH 0.5 M, incubated for 1 hour at room temperature, and then the column was rinsed with 3 BV of purified water.

220-300 mg of concentrated r-hIL-18BP obtained from capture step reported above under (1) were thawed and adjusted to pH to 8.5±0.1, conductivity 50±5 mS/cm by adding few drops of 35% ortho-phosphoric acid ($H_3PO_4$) and solid NaCl in the amount corresponding to about 0.35M.

The chromatographic column was first flushed with 5-4 BV (bed volumes) of acidified water until pH was <4.5. Then, the column was flushed with 3 BV of 0.2 M copper sulphate and 4 BV of acidified water until absorbance reached the baseline.

Then, the column was equilibrated by flushing 6 or more BV of equilibration buffer, 50 mM Sodium phosphate pH 8.5±0.1, 0.5 M NaCl, conductivity 50±5 mS/cm through the column. The pH and conductivity were checked and, and washing was continued if the parameters of the column's effluent are out of target values, i.e. pH 8.5±0.1, conductivity 50±5 mS/cm.

The starting material, i.e. post capture r-hIL-18BP prepared as above, was then loaded onto the column. After completion of sample loading, the column was flushed with 5-10 BV of equilibration buffer. These factions were discarded, since they contained only cell culture impurities.

Elution was started with 0.075 M ammonium acetate pH 9.0±0.1, conductivity 7.6±0.5 mS/cm. r-hIL-18BP started eluting as a main peak after about 0.5 BV from the start.

3-5 BV of the main peak were collected, the main peak starting when the on-line OD steeply increased. This fraction contained semi-purified r-hIL-18BP.

After completion of the elution, the column was flushed with 3-5 BV of regeneration buffer containing EDTA. The sampled fractions contained copper displaced from the resin, as well as cell culture impurities.

For sanitization, the column was flushed with at least 3 BV of NaOH 0.5 M, incubated for 1 hour, and then the column was rinsed with 3 BV of purified water. The column was then flushed with at least 3 BV of storage solution, 10 mM NaOH and is stored it at room temperature until the next cycle.

2.2. Step (b): HIC/IEC on MEP Hypercel

This step is carried out on MEP resin, a hydrophobic charge-induction chromatography resin, which is a mixture between hydrophobic interaction chromatography (HIC) and ion exchange chromatography (IEC).

Equipment

Chromatographic column: XK1.6×20 cm (Amersham Biosciences);

UV monitor (optical path Length 2.5 mm) equipped with a two channel recorder (Amersham Biosciences or equivalent);

Peristaltic pump (Minipuls Gilson or equivalent);

UV Spectrophotometer (Shimadzu or equivalent);

pH meter (Metrohm or equivalent);

Conductometer (Metrohm or equivalent);

Balance (MettlerToledo or equivalent).
Materials
Post IMAC r-hIL-18BP;
-MEP HyperCel® resin (BioSepra—Cypergen Biosystems);
Sodium Hydroxide pellets—(Merck);
Potassium Chloride—(Merck);
Ethylenediaminetetracetic acid—EDTA—(Fluka);
Sodium chloride—NaCl—Merck;
Purified water (Modulab or equivalent);
Di-Sodium hydrogen phosphate epta-hydrate—Merck;
Di-Sodium hydrogen phosphate monobasic di-hydrate—Merck;
Potassium Phosphate—Merck;
1-2 propandiol (Propylenglycol)—Merck;
85%-Ortho-PhosphoricAcid—Merck;
50% Sodium Hydroxide Solution—Baker.
Buffers and solutions
Equilibration buffer: Phosphate buffered saline (PBS) 1X pH 6.1±0.1, 1 NaCl, conductivity 95±5 mS/cm
Wash buffer: PBS 1X pH 6.1±0.1, conductivity 16±2 mS/cm
Elution buffer: 20 mM Phosphate buffer pH 8.4±0.1, 35% propylene glycol conductivity 1.1±0.3 mS/cm
Regeneration solution 1: Purified water
Regeneration solution 2: 100 mM EDTA
Sanitizing solution: 1M NaOH
The column was packed with MEP HyperCel® resin following the manufacturer's instructions.

Post IMAC IL-18BP, resulting from step (a), was supplemented with 1M NaCl under stirring up to a conductivity is 95±5 mS/cm.

For column sanitization, the column was flushed with at least 1 BV of NaOH 0.5 M, then rinsed with 3-5 BV of purified water.

For column equilibration, the column was flushed with 6 or more BV of equilibration buffer, PBS 1X pH 6.1±0.1, 1 NaCl, conductivity 95±5 mS/cm. pH and conductivity were checked, and washing continued if the parameters of the column's effluent are out of target values, i.e. pH 6.1±0.1, 1 NaCl, conductivity 95±5 mS/cm.

Then, the material was loaded with the material resulting from step (a).

After loading, the column was flushed with 6 BV of equilibration buffer PBS 1X pH 6.1±0.1, 1 NaCl, conductivity 95±5 mS/cm. This fraction was discarded, since it contained only cell culture impurities. In case of overloading of the column, this fraction may contain some r-hIL-18BP.

Then, the column was flushed with 10 BV of wash buffer PBS 1X pH 6.1±0.1, conductivity 16±2 mS/cm. This fraction was also discarded, containing only cell culture impurities. The fraction may contain some r-hIL-18BP in case of column overloading.

Then, elution was started with elution buffer 20 mM phosphate buffer pH 8.4±0.1, 35% propylene glycol conductivity 0.8±0.1 mS/cm. r-hIL-18BP started to elute as a main peak after about 0.5 BV from the start. 8-10 BV of the main peak were collected, starting from the steep increase in absorbance, approximately after the first 0.5 BV (discarded), according to the chromatographic profile. This eluate contained semi-purified r-hIL-18BP.

For regeneration, the column was flushed with at least 6 BV of regeneration solution 1, followed by 10 BV of regeneration solution 2. The column was left in regeneration solution overnight to further improve the regeneration effect. The column was then rinsed with at least 6 BV of purified water. These cell culture impurities containing fractions were discarded.

For sanitation, the column was flushed with at least 6 BV of 1M NaOH, the flow stopped for 1 hour, and the column then rinsed with at least 6 BV of purified water.

For storage, the column was flushed with at least 3 BV of storage solution, 0.1 M NaOH, and stored at room temperature until the next cycle.

2.3. Intermediate Step: ULTRAFILTRATION
Equipment
Ultrafiltration device Vivaflow 200, cut off 5000D (RC, PES or HydroSart)—Sartorius or equivalent;
Peristaltic pump type Masterflex or equivalent;
UV Spectrophotometer (Shimadzu or equivalent);
pH meter (Metrohm or equivalent);
Conductometer (Metrohm or equivalent);
Balance (Mettler Toledo or equivalent).
Materials
Post MEP r-hIL-18BP intermediate;
Sodium hydroxide pellets—Merck;
Purified water (Modulab or equivalent).
Solutions for Diafiltration
Purifed water by Modulab or Milli Q systems.
Sanitizing solution: 0.5 M NaOH
Procedure
The ultrafiltration step was performed at room temperature (+20±5° C.).

For ultrafilter sanitization, around 500 mL of 0.5 M NaOH were filtered for at least 30 minutes, and then the ultrafilter was rinsed with purified water until the permeate pH is below 7.5.

The post MEP fraction was diluted 1:2 with purified water, and filtered in the ultrafilter. The solution was concentrated to around 1-2/10 of the starting volume and the retentate fraction dialysed against purified water until the conductivity of the retentate was <100 μS/cm. Conductivity of the retentate was adjusted after dilution with water to a volume of around 150-200 mL.

The retentate fraction was collected and the ultrafilter washed with purified water. The wash fractions were collected and pooled with the retentate fraction (final volume 200-250 mL).

The ultrafilter was sanitizised by filtering 500 mL of 0.5 M NaOH, for not less than 30 minutes and following washing of the ultrafilter with purified water until the pH permeate was below 7.5.

The ultrafilter was stored in 0.05M NaOH at +4° C.±3° C. until the next cycle.

2.4. Step (c): IEC on CM Sepharose Fast Flow
Equipment
Chromatographic column: AC10/20 cm (Amersham Biosciences);
UV monitor (optical path Length 2.5 mm) equipped with two channel recorder (Amersham Biosciences or equivalent);
Peristaltic pump (Minipulse Gilson or equivalent);
UV Spectrophotometer (Shimadzu or equivalent);
pH meter (Metrohm or equivalent);
Conductometer (Metrohm or equivalent);
Balance (Mettler Toledo or equivalent).
Materials
Ultrafiltered r-hIL-18BP intermediate post MEP;
CM Sepharose FF resin (Amersham Biosciences);
Sodium hydroxide pellets—Merck;
MES (2-N-Morpholino)ethanesulfonic acid) (Sigma or equivalent);
Purified water (Modulab or equivalent);
Sodium chloride—Merck.

Buffers and Solutions

Pre-Equlibration buffer: 20 mM MES pH 5.0±0.5 conductivity 150±50 μsi/cm

Equilibration: 1 mM MES, pH 6.0±0.2 conductivity 45±15 μsi/cm

Regeneration solution:1.5M NaCl

Sanitizing solution: 0.5 M NaOH

Storage solution: 0.01M NaOH

The column was packed with CM Sepharose Fast Flow resin following the manufacturer's instructions.

Ultrafiltered r-hIL-18BP post MEP (see step (b)) was brought to pH 6.0±0.2 with some drops of 20 mM MES pH 5±0.5 and conductivity 100±15 μS/cm just before being loaded on the column.

For column sanitization, the column was flushed with 1 BV of NaOH 0.5 M and rinsed with 15-20 BV of purified water.

Then, the column was pre-equilibrated by flushing through the column 15-20 BV of 20 mM MES pH 5±0.5, conductivity 150±50 μS/cm. pH and conductivity were checked, and washing was continued if the parameters of the column's effluent were out of target values, i.e. pH 5.0±0.5, conductivity 150±50 μS/cm.

Then, the column was equilibrated by flushing through the column 5 or more BV of equilibration buffer, 1 mM MES pH 6.0±0.2, conductivity 45±15 μS/cm. pH and conductivity were checked, and washing continued if the parameters of the column's effluent were out of target values, pH 6.0±0.2, conductivity 45±15 μS/cm.

After equilibration, the r-hIL-18BP, prepared as above, was loaded. The flow through was collected as soon as the absorbance started to rise, since this fraction contains the semipurified r-hIL-18BP.

When sample loading was completed, the column was washed with 3-4 BV of equilibration buffer, 1 mM MES pH 6±0.2, conductivity 45±15 μS/cm, and flow-trough was continuously collected until the absorbance reached the baseline.

After collection, the solution was immediately brought to pH 9.1±0.1 by adding 50 mM solid sodium tetraborate. The collected fractions contain semipurified r-hIL-18BP.

For column regeneration, the column was flushed with at least 4 BV of regeneration buffer 1.5 M NaCl. Samples were taken and the fraction discarded. This fraction contains cell culture impurities and more basic isoforms of r-h IL-18BP.

For sanitization, the column was flushed with at least 3 BV of NaOH 0.5 M, the flow stopped for 1 hour, and then the column was rinsed with 3 BV of purified water.

For storage, the column was flushed with at least 3 BV of storage solution, and then stored until the next cycle.

2.5. Step (d): Hydrophobic interaction on Phenyl Sepharose FF HS

Equipment

Chromatographic column: XK16/20 (Amersham Biosciences);

UV monitor (optical path Length 2.5 mm) equipped with two channel recorder (Amersham Biosciences or equivalent), Peristaltic pump (Minipulse 2 Gillson or equivalent);

UV Spectrophotometer (Shimadzu or equivalent);

pH meter (Metrohm or equivalent);

Conductometer (Metrohm or equivalent);

Balance (Mettler Toledo or equivalent).

Materials r-hIL-18BP intermediate post CM;

Phenyl Sepharose FF HS resin (Amersham Biosciences);

Di-Sodium tetraborate decahydrate—Merck;

Ammonium Sulphate (Merck);

Purified water by Modulab or equivalent;

Sodium hydroxide pellets—Merck;

50% NaOH solution—J.T. Baker.

Buffers and Solutions

Equilibration buffer: 50 mM sodium borate 9.1±0.2, 0.9M Ammonium Sulphate conductivity 122±6 mS Elution buffer: 50 mM sodium borate 9.1±0.2, 0.15M Ammonium Sulphate conductivity 30±2 mS/cm Regeneration buffer: Purified water Sanitizing solution: 0.5 M NaOH The column was packed with Phenyl Sepharose FF HS resin following the manufacturer's instructions.

For preparation of the starting material, solid ammonium sulphate was added up to a concentration of 0.9M to post CM IL-18BP (result of step (c)). After dissolution of salt was completed, the material was brought to pH to 9.1±0.2 by adding 50% NaOH in solution.

For column sanitization, the column was flushed with at least 1 BV of NaOH 0.5 M and rinse the column with 6 BV of purified water.

The column was equilibrated by flushing through the column 5-7 or more BV of equilibration buffer: 50 mM sodium borate pH 9.1±0.2, 0.9 M Ammonium Sulphate conductivity 122±6 mS. pH and conductivity were checked, and washing continued if the parameters of the column's effluent were out of target values, i.e. pH 9.1±0.2, conductivity 122±6 mS.

The starting material, i.e. r-hIL-18BP post CM, was then loaded onto the column. When sample loading was completed, the column was flushed with 7-9 BV of equilibration buffer. This fraction contains residual cell culture impurities.

Elution was started with elution buffer 50 mM sodium borate pH 9.1±0.2, 0.15M Ammonium Sulphate conductivity 30±2 mS/cm. r-hIL-18BP started to elute as a main peak after about 0.5-0.8 BV from the start. 6-8 BV of the main peak was collected, starting from the increase in absorbance. This elution fraction contained semipurified r-hIL-18BP.

After completion of elution, the column was regenerated by rinsing the column with at least 3 BV of purified water. This fraction was discarded, since it contains cell culture impurities and aggregates forms of IL-18BP.

For sanitization, the column was flushed with at least 3 BV of 0.5 M NaOH, the flow stopped for 1 hour, and then the column was rinsed with 6 BV of purified water.

For storage, the column was flushed with at least 3 BV of storage solution, 10 mM NaOH, and the column stored at room temperature until the next cycle.

2.6. Step 5 (e):Reverse Phase on Source 30 RPC

Equipment

Chromatographic column: AC10//20 (Amersham Biosciences);

UV monitor (optical path length 2.5 mm) equipped with two channel recorder (Amersham Biosciences or equivalent);

Peristaltic pump (Minipulse 2 Gilson or equivalent);

UV Spectrophotometer (Shimadzu or equivalent);

FPLC system or equivalent to perform the linear gradient (Amersham Biosciences);

pH meter (Metrohm or equivalent);

Conductometer (Metrohm or equivalent).

Materials

IL-18BP post HIC

Source 30 RPC resin (Amersham Biosciences);

Sodium chloride—Merck;

Di-Sodium tetraborate decahydrate—Merck;

50% NaOH solution—Baker;

Purified water (Modulab or equivalent);

Acetonitrile—Merck;

Trifluoroacetic Acid—J.T. Baker;

Universal indicator pH 0-14—Merck.
Buffers and solutions:
Solution A: 0,1% TFA in water
Solution B: 0,1% TFA in ACN
Equilibration buffer: 50 mM Sodium Borate pH 9.1±0.2, conductivity 5±2 mS/cm
Sanitizing solution: 0.5 M NaOH The column was packed with Source 30 RPC resin following the manufacturer's instructions.

For column sanitization, the column was flushed in backflow with at least 3 BV of NaOH 0.5 M and then rinsed with 4-5 BV of purified water.

Then, the column was equilibrated by flush through the column (up-forward flow) 5-6 or more BV of equilibration buffer 50 mM Sodium Borate pH 9.1±0.2, conductivity 5±2 mS/cm. pH and conductivity were checked, and washing continued if the parameters of the column's effluent were out of target values, i.e. pH 9.1±0.2 and conductivity 5±2 mS/cm.

r-hIL-18BP post HIC (result of step (d)) at pH 9,1±0,2 conductivity 30±2 mS/cm was the starting material of this step. It was loaded onto the column, and when sample loading was completed, the column was flushed with 2-3 BV of equilibration buffer. This fraction was discarded.

Then, the column was washed with solution A until the pH of the column's effluent was below 4. This fraction was pooled with the first part of the elution gradient (before 28% of ACN). This fraction contains some residues of cell culture impurities and is thus discarded Elution was carried out in gradient mode using the combination of elution solution A and elution solution B as following detailed:

TABLE IV

| Time (minutes) | % A | % B | BV | Flow rate (mL/min) |
| --- | --- | --- | --- | --- |
| 0 | 100 | 0 | 0 | 5 |
| 50 | 65 | 35 | 22 | 5 |
| 60 | 65 | 35 | 26.5 | 5 |
| 65 | 20 | 80 | 29.0 | 5 |
| 75 | 20 | 80 | 33.0 | 5 | r-hIL-18BP started to elute at around 28-32% of solution B (see above in bold) and it was completely eluted within 60 minutes (35%B). The eluate was immediately brought to pH 8,0±0,5 by dilution 1:2 with 50 M sodium borate pH 9.1±0.2 and conductivity 5±2 mS/cm.

This fraction contains purified r-hIL-18BP.

Column regeneration was carried out at the end of the elution gradient. The regeneration fraction was collected according to the absorbance profile. This fraction contains residues of cell culture impurities and aggregates forms of IL-18BP.

For sanitization, the column was rinsed with 2-3 BV of water, flushed with at least 34 BV of NaOH and then the flow stopped for 1 hour. After that, the column was rinsed the column with 3-4 BV of purified water.

The column was flushed with at least 3 BV of storage solution, and stored until the next cycle.

3. Summary of Clearance of Host Cell Proteins from the IL-18BP Preparation

The amount of host cell proteins was measured by ELISA using a polyclonal antiserum that was raised in rabbit against CHO cell derived contaminants present in serum-free cell culture medium. The amount of host cell proteins is expressed as ppm (parts per million) of contaminating proteins in relation to purified IL-18BP. The amount of IL-18BP was measured by determination of the optical density (OD) at 280 nm (molar extinction coefficient $\epsilon=1.26$) in the purified preparation of IL-18BP, i.e. after the final purification step by Reverse Phase chromatography.

This analysis was carried out in the frame of three independent experiments.

TABLE V

| Clearance of host cell proteins | | | | |
| --- | --- | --- | --- | --- |
| Run | Start IMAC | Post IMAC | Post MEP | Post CM |
| 1 | 528966 ppm | 470600 ppm | 68400 ppm | >4000 ppm |
| 2 | 475322 ppm | 366800 ppm | 49800 ppm | 558 ppm |
| 3 | 230400 ppm | 236200 ppm | 89100 ppm | 641 ppm |

EXAMPLE 2

Modified Protocol for Purification of Recombinant, Human IL-18BP from Serum-Free Cho Cell Supernatant Example 1 was carried out as indicated above with the following modifications:

The capture step was carried out on Fractogel® TMAE HiCap®, purchased by Merck.

In step (a), the IMAC purification step on a Chelating Sepharose Fast Flow column, an additional washing step was added using 15 mM ammonium chloride in equilibration buffer.

In addition to this, in step (a) elution was carried out using 0.06 M ammonium acetate at pH 8.7.

In step (d), elution was started with elution buffer 50 mM sodium borate pH 9.1±0.2, 0.10 M Ammonium Sulphate.

Method: Determination of IL-18BP Specific Activity

Determination of the Biological Potency by KG-1 Cell in Vitro Bioassay

The biological characterisation of an r-hIL-18BP Reference Material was based on the evaluation of its ability to specifically bind r-hIL-18, neutralizing its biological activity on the human acute myelogenous leukemia cell line KG-1. This cell line is able to produce IFN-γ in response to human IL-18 plus human TNF-α in a dose-dependent manner, r-hIL-18BP thereby suppressing the production of IFN-γ.

Briefly, KG-1 cells at $1\times10^5$ cells/well were added to a 96 well plate already containing different concentrations of r-hIL-18BP in the presence of a fixed concentration of r-hIL18 (40 ng/ml in the well) plus a fixed concentration of r-hTNF-α (10 ng/ml in the well). The concentration of each of these two substances combined together was able to give the sub-maximal induction of production of IFN-γ on KG-1 cells. After 24 hr at 37° C., 5% $CO_2$, the plate was put at −20° C. in order to submit the treated cells to a freeze/thaw cycle before performing the immunoassay to determine the quantity of IFN-γ present in the cell supernatant. The cell supernatants were collected and human IFN-γ measured by means of a specific immunoassay (ELISA h-IFN-γ, Duo Set R&D Systems kit). The amount of IFN-γ produced by the treated cells was calculated by interpolating the y values (O.D.) on the IFN-γ Standard curve, provided with the kit, fitted by a Sigmoidal dose-response (4PL) Log/Log transformed, thus obtaining the x values (IFN-γ concentrations) (GraphPad Prism). The dilution of r-hIL-18BP Reference Material (ST1P01/r-hIL-18 BP) solution able to inhibit by 50% ($EC_{50}$) the amount of IFN-γ production induced by a fixed concentration of r-hIL-18+a fixed concentration of r-hTNF-α was defined as 1 Unit (U).

Ten independent assays were performed and each of the 10 dose-response curves was plotted by reporting on the y-axis the % of production of IFN-γ and on the x-axis the ST1P01/ r-hIL-18BP dilutions. The r-hIL-18BP dose-response curve generated in each experiment was first normalised by assuming equal to 0% and to 100% the lowest and the highest value of INF-γ, respectively.

The highest IFN-γ value was given by the r-hIL-18 plus r-hTNF-α combined concentrations in the absence of r-hIL-18BP, whereas the lowest was given by the higher r-hIL-18BP concentration tested. A sigmoidal dose-response with variable slope algorithm (4PL) was then applied to interpolate the normalised values and the $EC_{50}$ determined for each experiment.

The titre of the Reference Material was calculated in each assay as follows:

Titre (U/ml)=Reciprocal of the dilution at 50% of the response x pre-dilution The ST1P01/r-hIL-18BP final titre was calculated by averaging the 10 individual titres obtained in each experiment.

TABLE VI

Potency estimation of the ST1P01/r-hIL-18BP obtained in ten independent experiments

| Assay # | ST1P01/r-hIL-18BP (U/ml) | |
|---|---|---|
| 1 | | 794808 |
| 2 | | 884412 |
| 3 | | 1008216 |
| 4 | | 987696 |
| 5 | | 1021212 |
| 6 | | 980856 |
| 7 | | 1117314 |
| 8 | | 861156 |
| 9 | | 660402 |
| 10 | | 642618 |
| AVG | | 895869 |
| STDEV | | 157817 |
| CV % | | 17.6 |
| 95% CL | UCL | 1008760 |
| | LCL | 782973 |

The mean estimated potency of the Reference Material ST1P01/r-hIL-18BP resulted to be equal to 895869 U/ml with a CV % of 17.6.

KG-1 Cell in vitro Bioassay

The assay is carried out in 96/well plates.

| | 1 | 2 | 3 | 4 | 5 | 6 | 7 | 8 | 9 | 10 | 11 | 12 |
|---|---|---|---|---|---|---|---|---|---|---|---|---|
| A | C.C. | C.C. | C.C. | C.C. | C.C. | C.C. | C.C. | C.C. | C.C. | C.C. | C.C. | C.C. |
| B | 300 | 200 | 133 | 88.8 | 59.2 | 39.5 | 26.3 | 17.5 | 11.7 | 0 | IL-18 | TNF |
| C | 300 | 200 | 133 | 88.8 | 59.2 | 39.5 | 26.3 | 17.5 | 11.7 | 0 | IL-18 | TNF |
| D | $S1^1$ | $S1^1$ | $S2^1$ | $S2^1$ | $S3^1$ | $S3^1$ | | | | | | |
| E | $S1^2$ | $S1^2$ | $S2^2$ | $S2^2$ | $S3^2$ | $S3^2$ | | | | | | |
| F | | | | | | | | | | | | |
| G | | | | | | | | | | | | |
| H | | | | | | | | | | | | |

CC = Control Cells (Only Culture medium added);
TNF = r-hTNF-α at 10 ng/ml in the well
IL-18 = r-hIL-18 at 40 ng/ml in the well
0 = r-hIL-18 + r-hTNF-α at 40 + 10 ng/ml in the well, respectively
Rows B and C - r-hIL-18BP dose response curve step dilution 1:1.5
S1, S2 and S3 = Samples at 2 different concentrations falling in the linear part of the dose-response curve (2 replicates/sample) e.g. $S1^1$ = sample 1 at concentration 1; $S1^2$ = sample 1 at concentration 2).
The reported sample positions on the plate are an example.

Figure 2:
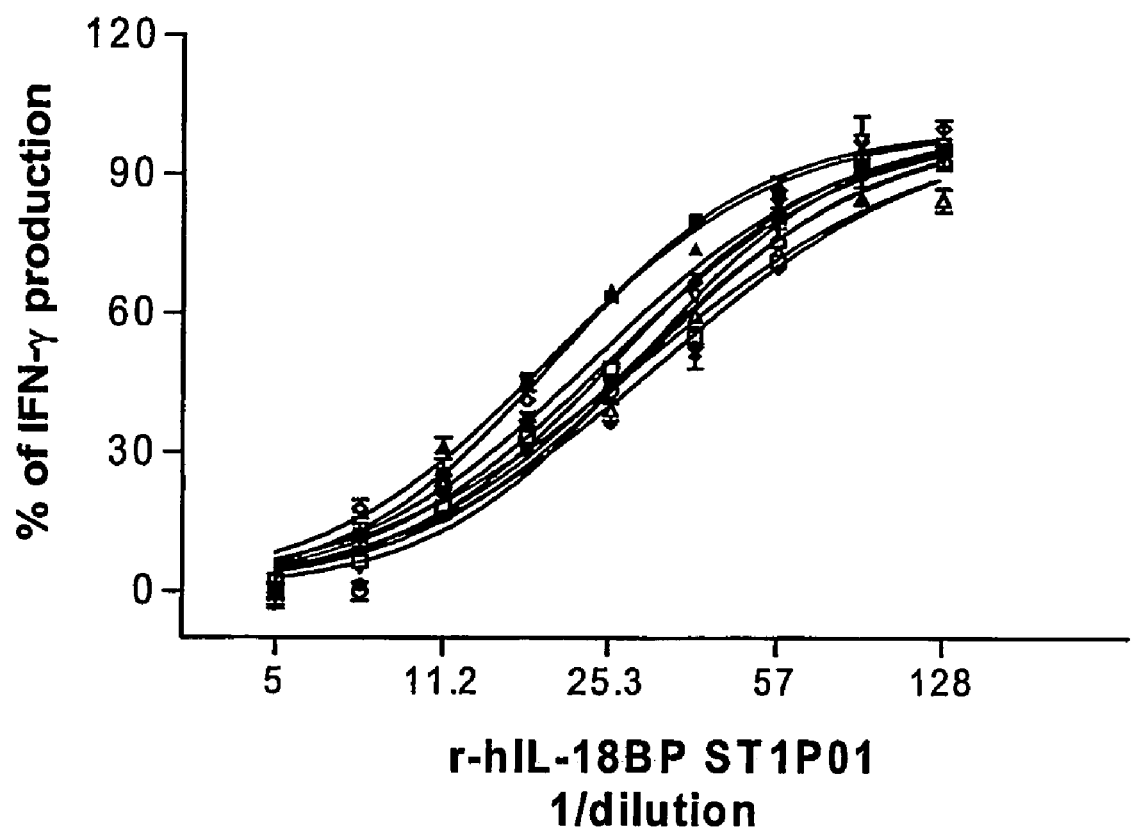
FIG. 2 shows the dose-response curves IL-18BP reference material in the Kg-1 in vitro bioassay in 10 independent experiments

FIG. 2 shows the dose-response curves of ST1P01/r-hIL-18BP by KG-1 in vitro bioassay obtained in 10 independent experiments.

The curves were normalised by assuming the lowest value of INF-γ equal to 0% and the highest value of INF-γ equal to 100%, respectively. The highest IFN-γ value was given by the r-IL-18 plus r-hTNF-α combined concentrations in the absence of r-hIL-18BP, whereas the lowest was given by the highest r-hIL-18BP concentration tested. A sigmoidal dose-response with variable slope algorithm (4PL) was then applied to interpolate the normalised values and the $EC_{50}$ determined for each experiment by means of GraphPad Prism.

The individual titres for the ST1P01/r-hIL-18BP obtained in each independent experiment together with the Standard deviation, the Coefficient of Variation (%) and the 95% Confidence Limits are reported below.

Add 50 μl of culture medium (500 ml IMDM supplemented with 20% FBS Heat inactivated 30 min at 56°, 5 ml 2-mercaptoethanol 3 mM, 5ml 2mM l-glutamine and 5 ml Pen/Strep; 10,000 U/ml /10,000 μg/ml) to the wells from 2 to 12 of rows B-C.

Add 150 μl of r-hIL-18BP Reference Material at 1500 ng/ml (300 ng/ml in the well) to the first well of rows B-C.

Using a multichannel pipette perform serial 1:1.5 dilutions by transferring 100 μl from the well in column 1 up to the well of column 9 (rows B-C), discarding the excess 100 μl from the well in column 9.

Add 50 μl of r-hIL-18BP sample prepared at one out of the 2 concentrations falling in the linear part of the dose response curve (e.g. $S1^1$ at 600 ng/ml corresponding to 120 ng/ml in the well) to the wells in columns 1-2 of row D (2 replicate).

N.B. the reported sample positions in the plate are provided as an example.

Repeat point 4 for the second (S1²) sample concentrations.
        Add 50 μl of r-hIL-18 at 200 ng/ml (40 ng/ml in the well) to all the wells of rows B-C except those in column 12 and to the wells containing the sample (e.g. columns 1-2 rows D-E).
        Add 50 μl of r-r-hTNF-α at 50 ng/ml (10 ng/ml in the well) to all the wells of rows B-C except those in column 11 and to the wells containing the sample (e.g. columns 1-2 rows D-E).
        Add 50 μl of culture medium to the wells in columns 11 and 12 of rows B-C
        Add 150 μl of culture medium to all the wells of row A (Control Cells wells).
        Add 100 μl of a KG-1 cell suspension at $1\times10^6$ cells/ml to all the wells of the 96 well plate.

NB: The final volume in the well is 250 μl; the final dilution of r-hIL-18BP 1:5. The cell suspension is prepared from a T75 flask containing not less than $20\text{-}24\times10^6$ cells (15 ml of culture medium).

Incubate the plate for 24 hr at 37° C., 5% $CO_2$
    Remove the plate from the incubator and put it at −20° C. until the immunoassay to determine the quantity of IFN-γ present in the cell supernatant is performed.
    The cell supernatant is collected and human IFN-γ measured by means of a specific immunoassay (ELISA h-IFN-γ, Duo Set R&D Systems kit).

NB: According to the r-hIL-18BP concentration added, perform, if needed, more than 1 dilution of the cell supernatant sample to be sure that the O.D. values measured are quantifiable on the IFN-γ Standard curve.

The ELISA was performed according to the general protocol provided with the kit with minor modifications:
    Number of washing step was increased: from 3 to 4 and from 4 to 5 for the last one.
    Block buffer prepared by adding 1% BSA in PBS (No sucrose, neither $NaN_3$ added).
    Reagent diluent prepared by adding 0.1% BSA and 0.05% Tween-20 in PBS instead of Tris-buffered Saline.

The amount of IFN-γ produced by the treated cells was calculated on the IFN-γ Standard curve (provided with the kit) Log/Log transformed and interpolated by means of a sigmoidal dose-response with variable slope algorithm (Graph Pad software).

Calculation of IL-18BP Specific Activity
    The specific activity of IL-18BP is calculated according to the following formula:

$$\frac{U}{mL} \div \frac{mg}{mL} = \frac{U}{mg}$$

Results:

The following tables indicate the results obtained for several parameters along the purification process as described in this example.

TABLE VII

Clearance of host cell proteins:

| Starting material (post-capture) | 291042 | 238636 | 336538 | 288739 |
|---|---|---|---|---|
| Post-IMAC | 96923 | 162619 | 148061 | 135867 |
| Post-MEP | 41563 | 43781 | 46708 | 44017 |
| Post-CM | 2138 | 2689 | 2550 | 2459 |
| Post-HIC | 372 | 1543 | 640 | 852 |
| Post-RPC | 83 | 111 | 121 | 105 |

TABLE VIII

Yield and HCP level:

| Average of 3 batches | Yield (%) | HCP (ppm) |
|---|---|---|
| Starting material (post-capture) | NA | 288739 |
| Post-IMAC | 91 | 135867 |
| Post-MEP | 98 | 44017 |
| Post-CM | 83 | 2459 |
| Post-HIC | 76 | 852 |
| Post-RPC | 70 | 105 |

TABLE IX

Main attributes of purified IL-18BP bulk (average 3 batches)

| Analysis of purified r-hIL18BP | Unit | level |
|---|---|---|
| Specific activity | U/mg | 18287 |
| HCP | ppm | 165 |

REFERENCES

1. Altschul S F et al, J Mol Biol, 215, 403-410, 1990
2. Altschul S F et al, Nucleic Acids Res., 25:389-3402, 1997
3. Boschetti, E., Jungbauer, Sep. Sci. & Tech. 2 No. 15, Acad. Press (2000) 53
4. Boschetti et al., Genetic Engineering Vol. 20, No. 13, July, 2000
5. Devereux J et al, Nucleic Acids Res, 12, 387-395, 1984.
6. Grantham et al., Science, Vol. 185, pp. 862-864 (1974)
7. Kim SH, Eisenstein M, Reznikov L, Fantuzzi G, Novick D, Rubinstein M, Dinarello CA. Structural requirements of six naturally occurring isoforms of the IL-18 binding protein to inhibit IL-18. Proc Natl Acad Sci U S A 2000;97: 1190-1195.
8. Novick, D, Kim, S-H, Fantuzzi, G, Reznikov, L, Dinarello, C, and Rubinstein, M (1999). Immunity 10, 127-136.
9. Pearson, Methods Enzymol. 1990;183:63-98.
10. J. Porath, J. Carlsson, I. Olsson, and G. Belfrage, Nature (London) 258, 598-599 (1975)
11. J. Porath and B. Olin, Biochemistry 22, 1621-1630 (1983)
12. Puren et al., Proc Natl Acad Sci U S A. 1999 Mar 2;96 (5):2256-61.
13. Urushihara, J Pediatr Surg. 2000 Mar; 35(3):446-9.
14. Vigers et al., Nature. 1997 Mar 13;386(6621):190-4.
15. WO9909063
16. WO0107480
17. WO0162285
18. WO0185201
19. WO02060479
20. WO02096456
21. WO03080104
22. WO02092008
23. WO02101049
24. WO03013577
25. WO92/13095
26. WO01/03737
27. U.S. Pat. No. 4,959,314
28. U.S. Pat. No. 4,588,585
29. U.S. Pat. No. 4,737,462
30. U.S. Pat. No. 5,116,943
31. U.S. Pat. No. 4,965,195
32. U.S. Pat. No. 4,879,111
33. U.S. Pat. No. 5,017,691
34. U.S. Pat. No. 4,904,584

The invention claimed is:

1. A process for the production of purified interleukin-18 binding protein (IL-18BP) comprising loading a fluid selected from urine or cell culture supernatant and containing IL-18BP onto a hydrophobic charge-induction chromatography resin equilibrated to a pH of 6.1±0.1 with a buffer and eluting the IL-18BP from said hydrophobic charge-induction chromatography resin with a buffer having a pH of 8.4±0.1.

2. The process according to claim 1, wherein the hydrophobic charge-induction chromatography resin is a 4-mercapto-ethyl-pyridine (MEP) resin.

3. The process according to claim 1, further comprising loading an eluate containing IL-18BP onto a chromatography resin selected from immobilized metal ion affinity chromatography resin, ion exchange chromatography resin, hydrophobic interaction chromatography resin and reverse phase chromatography resin.

4. The process according to claim 2, further comprising loading an eluate containing IL-18BP onto a chromatography resin selected from immobilized metal ion affinity chromatography resin, ion exchange chromatography resin, hydrophobic interaction chromatography resin and reverse phase chromatography resin.

5. The process according to claim 1, wherein said process comprises:
   (a) loading an IL-18BP containing fluid selected from urine or cell culture supernatant onto a metal ion affinity chromatography resin and eluting the IL-18BP from said resin;
   (b) loading the IL-18BP containing eluate of the metal ion affinity chromatography step onto a hydrophobic charge-induction chromatography resin and eluting the IL-18BP from said resin;
   (c) loading the IL-18BP containing eluate of the hydrophobic charge-induction chromatography step onto a cation exchange chromatography resin and eluting the IL-18BP from said resin;
   (d) loading the IL-18BP containing eluate of the cation exchange chromatography step onto a hydrophobic interaction chromatography resin and eluting the IL-18BP from said resin; and
   (e) loading the IL-18BP containing eluate of the hydrophobic interaction chromatography step onto a reverse phase chromatography resin and eluting the IL-18BP from said resin and recovering the eluted IL-18BP.

6. The process according to claim 1, further comprising one or more ultrafiltration steps.

7. The process according to claim 5, further comprising one or more ultrafiltration steps.

8. The process according to claim 1, comprising an initial capture step.

9. The process according to claim 8, wherein the capture step is carried out by strong anion exchange chromatography.

10. The process according to claim 9, wherein the capture step is carried out on a quaternary ammonium (Q) resin.

11. The process according to claim 9, wherein the capture step is carried out on a trimethylaminoethyl-derivatized (TMAE) resin.

12. The process according to claim 1, wherein said IL-18BP is human, recombinant IL-18BP.

13. The process according to claim 1, wherein the IL-18BP containing fluid is serum-free cell culture supernatant.

14. The process according to claim 1, wherein said process also comprises one or more steps comprising loading an eluate containing IL-18BP onto:
   (a) a metal ion affinity chromatography resin and eluting the IL-18BP from said resin;
   (b) a cation exchange chromatography resin and eluting the IL-18BP from said resin;
   (c) a hydrophobic interaction chromatography resin and eluting the IL-18BP from said resin; or
   (d) a reverse phase chromatography resin and eluting the IL-18BP from said resin.

15. The process according to claim 14, wherein said process comprises a combination of more than one of said steps.

16. A process for the production of purified interleukin-18 binding protein (IL-18BP) comprising:
   (a) loading an IL-18BP containing fluid selected from urine or cell culture supernatant onto a metal ion affinity chromatography resin and eluting the IL-18BP from said resin;
   (b) loading the IL-18BP containing eluate of the metal ion affinity chromatography step onto a hydrophobic charge-induction chromatography resin and eluting the IL-18BP from said resin;
   (c) loading the IL-18BP containing eluate of the hydrophobic charge-induction chromatography step onto a cation exchange chromatography resin and eluting the IL-18BP from said resin;
   (d) loading the IL-18BP containing eluate of the cation exchange chromatography step onto a hydrophobic interaction chromatography resin and eluting the IL-18BP from said resin; and
   (e) loading the IL-18BP containing eluate of the hydrophobic interaction chromatography step onto a reverse phase chromatography resin and eluting the IL-18BP from said resin and recovering the eluted IL-18BP.

17. The process according to claim 16, wherein said:
   (a) metal ion affinity chromatography resin is a chelating sepharose column containing chelated $Zn^{2+}$ ions and said IL-18BP is eluted with a 0.075 M ammonium acetate or in 0.06 M ammonium acetate buffer at a pH of 9.0±0.5;
   (b) said hydrophobic charge-induction chromatography resin is a 4-mercaptoethylpyridine derivative (MEP) column and said IL-18BP is eluted with a buffer comprising 20 mM phosphate buffer and 35% propylene glycol at a pH of 8.4 ±0.1;
   (c) said cation exchange chromatography resin is a carboxymethyl-sepharose (CM) column and said IL-18BP is collected in a flow-through eluted with a 1 mM N-morpholinoethanesulfonic acid (MES) buffer at a pH of 6.0±0.2;
   (d) said hydrophobic interaction chromatography resin is a phenyl sepharose column and said IL-18BP is eluted with a buffer comprising 50 mM sodium borate and 0.15M ammonium sulfate at a pH of 9.1±0.2; and
   (e) said reverse phase chromatography resin is a Source 30 reverse phase chromatography column and said IL-18BP is eluted using a buffer gradient, said buffer gradient comprising a first buffer comprising 0.1% trifuoroacetic acid (TFA) in water and a second buffer comprising 0.1% trifluoroacetic acid (TFA) in acetonitrile at a pH of 9.1±0.2.

18. The process according to claim 16, further comprising one or more ultrafiltration steps.

* * * * *

UNITED STATES PATENT AND TRADEMARK OFFICE
CERTIFICATE OF CORRECTION

| | | |
|---|---|---|
| PATENT NO. | : 7,820,800 B2 | Page 1 of 2 |
| APPLICATION NO. | : 10/576372 | |
| DATED | : October 26, 2010 | |
| INVENTOR(S) | : Rossi et al. | |

It is certified that error appears in the above-identified patent and that said Letters Patent is hereby corrected as shown below:

Column 6,
Line 33, "at. pH" should read --at pH--.

Column 11,
Lines 38-39, "thereof. "Functional derivatives" as used" should read
--thereof.
"Functional derivatives" as used--.

Column 14,
Line 67, "is not any" should read --is not in any--.

Column 15,
Line 12, "meaning an range" should read --meaning and range--.
Lines 32-33, "adding few drops" should read --adding a few drops--.

Column 16,
Lines 18-19, "adding few drops" should read --adding a few drops--.
Lines 21-22, "with 5-4 BV" should read --with 5-6 BV--.
Lines 29-30, "checked and, and washing" should read --checked and washing--.

Column 17,
Line 4, "-MEP" should read --MEP--.

Column 18,
Line 64, "(2-N-Morpholino)ethanesulfonic acid)" should read
--(2-[N-Morpholino]ethanesulfonic acid)--.

Column 19,
Line 57, "2 Gillson" should read --2 Gilson--.

Signed and Sealed this
Eighteenth Day of January, 2011

David J. Kappos
*Director of the United States Patent and Trademark Office*

CERTIFICATE OF CORRECTION (continued)
U.S. Pat. No. 7,820,800 B2

<u>Column 21,</u>
Line 56, "34 BV" should read --3-4 BV--.
Lines 57-58, "the column was rinsed the column with" should read --the column was rinsed with--.